United States Patent [19]

Fertel et al.

[11] Patent Number: 5,003,103
[45] Date of Patent: Mar. 26, 1991

[54] PREPARATION OF 2-CHOLORO-4,5-DIFLUOROBENZOIC ACID FROM 4,5-DIFLUOROPHTHALIC ANHYDRIDE OF 4,5-DIFLUOROPHTHALIC ACID

[75] Inventors: Lawrence B. Fertel, Buffalo; Henry C. Lin, Grand Island, both of N.Y.

[73] Assignee: Occidental Chemical Corporation, Niagara Falls, N.Y.

[21] Appl. No.: 532,763

[22] Filed: Jun. 4, 1990

Related U.S. Application Data

[63] Continuation-in-part of Ser. No. 439,228, Nov. 20, 1989, Pat. No. 4,937,377.

[51] Int. Cl.$^5$ .............................................. C07C 51/38
[52] U.S. Cl. ..................................................... 562/479
[58] Field of Search ......................................... 562/479

[56] References Cited

U.S. PATENT DOCUMENTS 1,956,718  5/1934  Jaeger .................................. 562/479
4,935,541  6/1990  O'Reilly .............................. 562/479

FOREIGN PATENT DOCUMENTS 223420   5/1982   European Pat. Off. .
272671   7/1988   European Pat. Off. .
2914915  10/1980  Fed. Rep. of Germany .
123487   7/1985   Japan .

*Primary Examiner*—Paul J. Killos
*Attorney, Agent, or Firm*—James F. Tao; John H. Engelmann

[57] ABSTRACT

2-Chloro-4,5-difluorobenzoic acid may be prepared by decarboxylating 4,5-difluorophthalic anhydride or 4,5-difluorophthalic acid by heating in N-methyl-2-pyrrolidone or dimethyl acetamide optionally using copper, copper oxide, copper salts, or halides or salts of Zn, Cd, Ag and Ni as a catalyst to form 3,4-difluorobenzoic acid, reacting said 3,4-difluorobenzoic acid with a mixture of nitric and sulfuric acids to form 2-nitro-4,5-difluorobenzoic acid, reacting said 2-nitro-4,5-difluorobenzoic acid with elemental chlorine at a temperature of between 185° and 195° C. to form 2-chloro-4,5-difluorobenzoic acid.

36 Claims, No Drawings

PREPARATION OF 2-CHOLORO-4,5-DIFLUOROBENZOIC ACID FROM 4,5-DIFLUOROPHTHALIC ANHYDRIDE OF 4,5-DIFLUOROPHTHALIC ACID

This invention is a Continuation-In-Part of U.S. Ser. No. 07/439,228, now U.S. Pat. No. 4,937,377.

BACKGROUND OF THE INVENTION

This invention relates to a method for the preparation of 2-chloro-4,5-difluorobenzoic acid from 4,5,-difluorophthalic anhydride or 4,5-difluorophthalic acid. 2-Chloro-4,5-difluorobenzoic acid is a known compound, and a useful chemical intermediate. For example, 2-chloro-4,5-difluorobenzoic acid is a valuable intermediate in the synthesis of quinolone antibacterials.

Chlorodenitration reactions are known. For example, Ponomarenko discloses (J. Gen. Chem USSR (Engl. Tran.) that 3-nitrophthalic anhydride reacts with chlorine at a temperature of 230°-250° C. to form 3-chlorophthalic anhydride. It might be expected that this process would be prove troublesome if applied to a nitrobenzoic acid because the single carboxylic acid group decarboxylates more readily then the phthalic anhydride.

3,4-Difluorobenzoic acid has been prepared by the oxidation of the corresponding toluene derivative (G. Valkanas, J. Org. Chem., 27 (1962) 2923).

Many examples of decarboxylation reactions have been reported. Basic substances have been used to catalyze such reactions. For example, it is disclosed in D. S. Tarbell, et al Org. Syn., Coll. Vol. III (1955) 267, that 3,5-dichloro-4-hydroxybenzoic acid may be decarboxylated by vigorous heating in N,N-dimethylaniline. It is disclosed in A. Singer and S. M. McElvane, Org. Syn., Coll. Vol. 11 (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., Coll. Vol. III (1955) 471 disclose the use of a copper oxide catalyst for the decarboxylation of imidazole 4,5-dicarboxylic acid.

Some compounds may be decarboxylated without catalysts. For example, C. Wang, Bul. Inst. Kim. Acad. Sinica, no. 2156 (1972), as abstracted in Chem. Abstracts (CA79 (15):91729), discloses that tetrachloro or tetrabromophthalic acids, or their anhydrides, may be decarboxylated to the corresponding benzoic acids when refluxed in dimethyl formamide. 3-nitrophthalic acid underwent a similar reaction.

Decarboxylation is not always a predictable reaction. For example, A. S. Sultanov, J. Gen. Chem. (USSR) 16 1835 (1946) as abstracted in CA 41:6223(e) discloses that salicylic acid may be decarboxylated by autoclaving the acid in the presence of copper bronze and benzene at 170° C. The acid alone decarboxylates at 205° C., while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported. 3,4,5,6-Tetrafluorophthalic acid decarboxylates under certain conditions to yield 2,3,4,5-tetrafluorobenzoic acid. For example, Japanese Patent JP 61/85349 A2[86/85349] as abstracted in Chem. Abstracts (CA105:152719r), discloses that the reaction may be conducted in an aqueous medium at 150° to 230° C. The reaction may be carried out at a lower temperature (100° to 250° C.) in the presence of copper, zinc, cadmium, iron, cobalt, nickel, other oxides, hydroxides and/or carbonates. Japanese Patent Application 86/103,317 as abstracted in Chem. Abstracts (CA105 (22):193368u), discloses that the above reaction may be conducted in an aqueous medium at a pH of 0.7-2.2 at a temperature of 100°-200° C. The pH of the medium is adjusted by acidifying with sulfuric acid and partial neutralization with calcium hydroxide. Japanese Patent 63/295529m A2[88/295529] as abstracted in Chem. Abstracts (CA 111 (3): 23221X), discloses that the reaction may be conducted at 130° in tri-butylamine.

Yacobsen, O. J. discloses in Zh. Obsch. Khim. 36 (1966) page 139 (as appearing in Journal of General Chemistry of the U.S.S.R. translated from Russian 36 (1966) page 144), that 2,3,4,5-tetrafluorophthalic acid may be decarboxylated to yield 2,3,4,5-tetrafluorobenzoic acid by heating for one hour at 145° C. in dimethyl formamide solvent.

Japanese Patent JP 01/52737 as abstracted in Chem. Abstract (CA)111 (14):117305e discloses the preparation of 2,4,5-trifluorobenzoic acid by the decarboxylation of 3,4,6-trifluorophthalic acid in a liquid medium at a temperature of 80°-250° C.

Under slightly more vigorous conditions, Japanese Patent Application 61/43130 A2[86/43130] as abstracted in Chem. Abstracts (CA106 (1):46295), discloses that 3,4,5,6-tetrafluorophthalic acid may be completely decarboxylated to 1,2,3,4-tetrafluorobenzene. The conditions for complete decarboxylation are in an aqueous medium from 210° to 300° C. with the optional presence of a catalyst.

Japanese Patent Application 86/290399 as abstracted in Chem. Abstracts (CA109 (19) 170038e), discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

SUMMARY OF THE INVENTION 2-chloro-4,5-difluorobenzoic acid may be prepared by decarboxylating 4,5-difluorophthalic anhydride or 4,5-difluorophthalic acid to form 3,4-difluorobenzoic acid in N-methyl-2-pyrrolidone, quinoline, or dimethyl acetamide optionally using copper, copper oxide, copper salts, or halides and salts of Zn, Cd, Ag and Ni as a catalyst, treating said 3,4-difluorobenzoic acid with a mixture of nitric and sulfuric acids, to produce 2-nitro-4,5-difluorobenzoic acid, and treating said 2-nitro-4,5-difluorobenzoic acid with elemental chlorine to form 2-chloro-4,5-difluorobenzoic acid.

DETAILED DESCRIPTION OF THE INVENTION

The present invention provides a process for producing 2-chloro-4,5-difluorobenzoic acid. In this process, 4,5,-difluorophthalic anhydride or 4,5-difluorophthalic acid is decaboxylated to form 3,4-difluorobenzoic acid. The decarboxylation reaction is conducted in N- methylpyrrolidone, quinoline, or dimethyl acetamide. Optionally, copper, copper compounds, or halides and salts of Zn, Cd, Ag and Ni may be used as catalysts in this reaction. The 3,4-difluorobenzoic acid is nitrated to form 2-nitro-4,5-difluorobenzoic acid, which is then chlorodenitrated to produce 2-chloro-4,5-difluorobenzoic acid.

4,5-Difluorophthalic anhydride may be readily prepared by the reaction of 4,5-dichlorophthalic anhydride with potassium fluoride as disclosed in U.S. Pat. No. 4,374,266 (Example I). The acid may be readily prepared by reacting the anhydride with water.

The decarboxylation of 4,5-difluorophthalic anhydride proved to be difficult, since previously known methods of decarboxylation led to a low yield of the desired product along with numerous by-products. The following chart illustrates the decarboxylation methods which were tested. The percentage product shown in the results were those obtained by gas chromatographic analysis, DFBA stands for 3,4-difluorobenzoic acid. s.m. stands for starting material.

| Decarboxylation of 4,5-difluorophthalic anhydride | |
|---|---|
| Conditions | Results |
| (1) 150–190°/95% $H_2SO_4$ | No Reaction |
| (2) 150 N-methyl-2-pyrrolidone No catalyst | No Reaction |
| (3) 140°/DMF/12 hours No catalyst | 0% DFBA/50% s.m.; 50% other |
| (4) 150° DMAc/$Cu_2O$/22 hours | 19% DFBA/31% s.m./ 31% other |
| (5) 150° DMAc/CuO/27 hours | 27% DFBA/9% s.m./ 44% other |
| (6) 150° DMAc/CuO/22 hours | 40% DFBA/12% s.m./ 36% other |
| (7) 200° Quinoline/Cu/3 hours | 42% DFBA/51% s.m./ 7% other |
| (8) 190° N-methyl-2-pyrrolidone/ 7 hours | 4% DFBA/74% s.m. 22% other |
| (9) 190° DMSO/10%$Cu_2O$/5 hours | many products |
| (10) 190° DMSO/10%CuO/5 hours | many products |

Similarly, the decarboxylation of 4,5-difluorophthalic acid provided to be difficult as well. The decarboxylation was attempted using several methods. The results are shown in the chart below:

| Reactions with 4,5-difluorophthalic Acid | |
|---|---|
| Conditions | Results |
| (1) 100° 10% $H_2SO_4$/18 hours | No Reaction |
| (2) 200° 85% $H_2SO_4$ | No Reaction |
| (3) 170° DMSO/18 hours | No Reaction |
| (4) 150° Sulfolane | No Reaction |
| (5) 150° DMSO/LiCl/12 hours | No Reaction |
| (6) 150° DMSO/NaCl/12 hours | No Reaction |
| (7) 125° DMAc/No Catalyst | No Reaction |
| (8) 150° DMAc/22 hours | 0% DFBA, 9% s.m., 91% other |
| (9) 150° DMAc/CuO | 47% DFBA, 2% s.m. 51% other |
| (10) 150° DMAc/$Cu_2O$/22 hours | 69% DFBA, 0% s.m., 31% other |
| (11) 125° DMAc/CuO/22 hours | 60% DFBA, 3% s.m., 37% other |
| (12) 125° DMAc/$Cu_2O$/22 hours | 70% DFBA, 8% s.m., 22% other |

Surprisingly, we have found that 4,5-difluorophthalic anhydride and 4,5-difluorophthalic acid may be selectively decarboxylated in N-methyl-pyrrolidone, dimethyl acetamide or quinoline to yield 3,4-difluorobenzoic acid.

The selective decarboxylation of 4,5-difluorophthalic acid or 4,5-difluorophthalic anhydride to yield 3,4-difluorobenzoic acid, may be conducted without a catalyst. However, if no catalyst is used, decarboxylation is conducted in a temperature range of 175°–215° C. In addition, without a catalyst, reactions are rather slow. The decarboxylation is preferably conducted using a copper catalyst such as Cu, $Cu_2O$, CuO, $CuSO_4$, $CuCl_2$, CuCl, $CuF_2$, Cu and $Cu(OH)_2$. In addition, halides and salts of Zn, Cd, Ag and Ni may be used as catalysts. With a catalyst, the reaction may be conducted in a temperature range from about 125°–215° C., with the preferred range being 125°–150° C. The catalyst shows some effect at concentrations as low as 1%. However, it is preferred to use between 5 and 10 percent by weight of catalyst. At any point in the reaction, the degree of starting materials to product can readily be judged by gas chromatographic analysis. However, the reaction is reproducible and once convenient conditions, within the scope of this invention, have been established for conducting the reaction, the gas chromatographic analysis need not be conducted routinely.

The preferred method for conducting this decarboxylation is to use N-methyl-2-pyrrolidone as a solvent, 5 to 10% CuO as a catalyst, and to heat the solution for a period of 2–3 hours. Under these conditions the anhydride and the acid are fully converted to the desired product, and there seem to be no side products detectable by gas chromatography.

The difluorobenzoic acid may be isolated from the reaction mixture by acidifying the mixture and extracting with a suitable solvent such as ethyl acetate or diethyl ether. Evaporation of the solvent yields crude difluorobenzoic acid which may be recrystallized/decolorized by using water and activated carbon.

3,4-Difluorobenzoic acid may be nitrated in a mixture of nitric and sulfuric acids. The nitration is best conducted at a low temperature to avoid decarboxylation of the benzoic acid. In addition, it is a good idea to avoid an excess of nitric acid in conducting the nitration in order to avoid the formation of side products. The preferred procedure is to dissolve the 3,4-difluorobenzoic acid in sulfuric acid, and cool the solution on an ice bath. Nitric acid is then added slowly to the mixture. The mixture is then warmed to room temperature and stirred until the reaction is complete. The reaction mixture is then poured over ice, and the product, 2-nitro-4,5-difluorobenzoic acid recovered.

2-Nitro-4,5-difluorobenzoic acid may be treated with elemental chlorine to form 2-chloro-4,5-difluorobenzoic acid. The reaction between 2-nitro-4,5-difluorobenzoic acid and elemental chlorine may be conducted without a solvent, or in a wide variety of organic solvents. Any solvent in which the 2-nitro-4,5-difluorobenzoic acid is reasonably soluble, and which is stable to elemental chlorine at temperatures slightly under 200° C., is suitable as a solvent for the reaction. For example, trichlorobenzene isomers and chlorinated benzotrichlorides may be used as solvents. The preferred solvent, if a solvent is to be used, is 1,2,4-trichlorobenzene. The temperature at which the reaction is run is critical. If the reaction is run below 180° C., the rate of reaction is too slow to be practical. On the other hand, at 200° C., the reaction yields a high percentage of dimeric products. The ideal temperature range for the reaction is 185°–195° C.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLES

Example 1 Preparation of 3,4-difluorobenzoic acid 4,5-difluorophthalic anhydride (0.5 grams, 2.7 mmole) was added to a slurry of cupric oxide (5% by weight of starting material) in 5 ml. of N-methyl-2-pyrrolidone. n-tridecane (0.25 grams) was added as an internal standard. The mixture was heated to 190° C. for 3 hours, at which time GC analysis indicated complete consumption of the starting material and conversion to 3,4-difluorobenzoic acid in an 85% yield, based upon the internal standard, corrected for response factors.

Example 2 Preparation of 3,4-difluorobenzoic acid 4,5-difluorophthalic acid (0.55 grams, 2.7 mmole) was added to a slurry of cupric oxide (10% by weight of starting material) in 5 ml. of N-methyl-2-pyrrolidone solvent. n-tridecane (0.25 grams) was added as an internal standard. The mixture was heated to 190° C. for 3 hours, at which time GC analysis indicated complete consumption of the starting material and conversion to 3,4-difluorobenzoic acid in an 87% yield, based upon the internal standard, corrected for response factors.

Example 3 Preparation of 3,4-difluorobenzoic acid 4,5-difluorophthalic acid (0.55 grams, 2.7 mmole) was added to a slurry of cupric oxide (10% by weight) in dimethyl acetamide. The mixture was heated to 125° C. for 24 hours. Analysis by gas chromatography showed 70% 3,4-difluorobenzoic acid, 8% starting material and 25% other products.

Example 4 Preparation of 3,4-difluorobenzoic acid

Using a procedure similar to that of Example 3, 0.55 grams, (2.7 mmole) of 4,5-difluorophthalic acid was added to dimethyl acetamide. 10% $Cu_2O$ as a catalyst was added and the solution was heated at 125° C. for 24 hours. The yield of 3,4-difluorobenzoic acid was 70% (by gas chromatography).

Example 5 Preparation of 3,4-difluorobenzoic acid

Using a procedure similar to that of Example 3, 0.55 grams, (2.7 mmole) of 4,5-difluorophthalic acid was added to dimethyl acetamide. $Cu_2O$ as a catalyst was added and the solution was heated at 150° C. for 22 hours. The yield of 3,4-difluorobenzoic acid was 69% (by gas chromatography).

Example 6 Preparation of 3,4-difluorobenzoic acid

Using a procedure similar to that of Example 3, 0.5 grams, (2.7 mmole) of 4,5-difluorophthalic anhydride was added to N-methylpyrrolidone. 1% $Cu_2O$ as a catalyst was added and the solution Was heated at 190° C. for 30 hours. The yield of 3,4-difluorobenzoic acid was 82% (by gas chromatography).

Example 7 Preparation of 3,4-difluorobenzoic acid

Using a procedure similar to that of Example 3, 0.5 grams, (2.7 mmole) of 4,5-difluorophthalic anhydride was added to N-methylpyrrolidone and the solution was heated at 190° C. for 30 hours. The yield of 3,4-difluorobenzoic acid was 79% (by gas chromatography).

Example 8 Nitration of 3,4-difluorobenzoic acid

Into 100 mL of 96% sulfuric acid was placed 3,4-difluorobenzoic acid(11.95 g, 0.0756 mol). The solution was stirred at room temperature until the DFBA was dissolved, and then cooled to 0° C. Nitric acid (7.9 g of 90% fuming) was added dropwise to the cooled mixture. After addition, the solution was warmed to room temperature and stirred until completion of the reaction. After drying, 11.88 g of 2-nitro-4,5-difluorobenzoic acid was isolated. The material was identified by GCMS and $^{19}F$ NMR analysis. An additional 2.41 g of product was obtained by extraction of the acid washes and removal of the solvent.

Example 9 Chlorodenitration of 2-nitro-difluorobenzoic acid to 2-chloro-4,5-difluorobenzoic acid in a solvent 8.05 g of 2-nitro-4,5-difluorobenzoic acid was added to 10 mL of 1,2,4-trichlorobenzene. The solution Was heated to 190° C., at which time chlorine gas was sparged through the reaction mixture. After 10 h, GC analysis indicated complete conversion of the starting material to the product. The solution was cooled, at which time the product came out of solution. After filtering, the solid material was washed with a small amount of hexane. 4.69 g of product was recovered. The material was identified as 2-chloro-4,5-difluorobenzoic acid by GCMS and $^{19}F$ NMR analysis.

Example 10 High temperature chlorodenitration of 2-nitro-difluorobenzoic acid to 2-chloro-4,5-difluorobenzoic acid in a solvent The reaction between 2-nitro-4,5-dichlorobenzotrifluoride and chlorine in 1,2,4-trichlorobenzene solvent was repeated as described above; however, the internal temperature was kept at 200°–210° C. After four hours, a sample was taken. GC analysis indicated the formation of significant amounts of high molecular weight by-products. Mass spectrometric analysis indicated that these by-products were various dimeric species.

Example 11 Chlorodenitration of 2-nitro-difluorobenzoic acid to 2-chloro-4,5-difluorobenzoic acid without solvent.

As in the above example, 3.0 g of 2-nitro-4,5-difluorobenzoic acid was heated to 190° C. and sparged with chlorine gas. No solvent was added. After 3 h, GC analysis indicated formation of 2-chloro-4,5-difluorobenzoic acid.

We claim:

1. A process for the preparation of 2-chloro-4,5-difluorobenzoic acid which comprises dissolving a starting material selected from the group consisting of 4,5-difluorophthalic anhydride and 4,5-difluorophthalic acid in a solvent selected from the group consisting of dimethyl acetamide, N-methyl-2-pyrrolidone and quinoline to form a solution, and heating said solution at a temperature between 175° and 215° C. to form 3,4-difluorobenzoic acid, reacting said 3,4-difluorobenzoic acid with a mixture of nitric and sulfuric acids to form 2-nitro-4,5-difluorobenzoic acid; and reacting said 2-nitro-4,5-difluorobenzoic acid with elemental chlorine at a temperature of between 185° and 195° C. to form 2-chloro-4,5-difluorobenzoic acid.

2. A process according to claim 1 wherein the reaction between 2-nitro-4,5-difluorobenzoic acid and elemental chlorine is conducted in the presence of a solvent.

3. A process according to claim 2 wherein said solvent is trichlorobenzene.

4. A process according to claim 2 wherein said solvent is a halogenated benzotrichloride.

5. A process for the preparation of 2-chloro-4,5-difluorobenzoic acid which comprises dissolving 4,5-difluorophthalic anhydride in a solvent selected from the group consisting of dimethyl acetamide N-methyl-2-pyrrolidone and quinoline to form a solution, adding to the solution a catalytic amount of a catalyst selected from the group consisting of Cu, $Cu_2O$, CuO, copper salts, and oxides and salts of Zn, Cd, Ag and Ni and heating said solution at a temperature between 120° and 215° C. to form 3,4-difluorobenzoic acid, reacting said 3,4-difluorobenzoic acid with a mixture of nitric and sulfuric acids to form 2-nitro-4,5-difluorobenzoic acid; and reacting said 2-nitro-4,5-difluorobenzoic acid with elemental chlorine at a temperature of between 185° and 195° C. to form 2-chloro-4,5-difluorobenzoic acid.

6. A process according to claim 5 wherein the reaction between 2-nitro-4,5-difluorobenzoic acid and elemental chlorine is conducted in the presence of a solvent.

7. A process according to claim 6 wherein said solvent is trichlorobenzene.

8. A process according to claim 7 wherein said solvent is a halogenated benzotrichloride.

9. A process according to claim 5 wherein said catalyst is metallic copper.

10. A process according to claim 9 wherein the reaction between 2-nitro-4,5-difluorobenzoic acid and elemental chlorine is conducted in the presence of a solvent.

11. A process according to claim 10 wherein said solvent is trichlorobenzene.

12. A process according to claim 10 wherein said solvent is a halogenated benzotrichloride.

13. A process according to claim 5 wherein the catalyst is $Cu_2O$.

14. A process according to claim 13 wherein the reaction between 2-nitro-4,5-difluorobenzoic acid and elemental chlorine is conducted in the presence of a solvent.

15. A process according to claim 14 wherein said solvent is trichlorobenzene.

16. A process according to claim 14 wherein said solvent is a halogenated benzotrichloride.

17. A process according to claim 5 wherein the catalyst is CuO.

18. A process according to claim 17 wherein the reaction between 2-nitro-4,5-difluorobenzoic acid and elemental chlorine is conducted in the presence of a solvent.

19. A process according to claim 18 wherein said solvent is trichlorobenzene.

20. A process according to claim 18 wherein said solvent is a halogenated benzotrichloride.

21. A process for the preparation of 2-nitro-4,5-difluorobenzoic acid which comprises heating dissolving 4,5-difluorophthalic acid in a solvent selected from the group consisting of dimethyl acetamide, N-methyl-2-pyrrolidone and quinoline to form a solution, adding to the solution a catalytic amount of a catalyst selected from the group consisting of Cu, $Cu_2O$, and CuO, copper salts, and oxides and salts of Zn, Cd, Ag and Ni and heating said solution at a temperature between 120° C. to 215° C. to form 3,4-difluorobenzoic acid, reacting said 3,4-difluorobenzoic acid with a mixture of nitric and sulfuric acids to form 2-nitro-4,5-difluorobenzoic acid; and reacting said 2-nitro-4,5-difluorobenzoic acid with elemental chlorine at a temperature of between 185° and 195° C. to form 2-chloro-4,5-difluorobenzoic acid.

22. A process according to claim 21 wherein the reaction between 2-nitro-4,5-difluorobenzoic acid and elemental chlorine is conducted in the presence of a solvent.

23. A process according to claim 22 wherein said solvent is trichlorobenzene.

24. A process according to claim 22 wherein said solvent is a halogenated benzotrichloride.

25. A process according to claim 21 wherein said catalyst is metallic copper.

26. A process according to claim 25 wherein the reaction between 2-nitro-4,5-difluorobenzoic acid and elemental chlorine is conducted in the presence of a solvent.

27. A process according to claim 26 wherein said solvent is trichlorobenzene.

28. A process according to claim 26 wherein said solvent is a halogenated benzotrichloride.

29. A process according to claim 21 wherein the catalyst is $Cu_2O$.

30. A process according to claim 29 wherein the reaction between 2-nitro-4,5-difluorobenzoic acid and elemental chlorine is conducted in the presence of a solvent.

31. A process according to claim 30 wherein said solvent is trichlorobenzene.

32. A process according to claim 30 wherein said solvent is a halogenated benzotrichloride.

33. A process according to claim 21 wherein the catalyst is CuO.

34. A process according to claim 33 wherein the reaction between 2-nitro-4,5-difluorobenzoic acid and elemental chlorine is conducted in the presence of a solvent.

35. A process according to claim 34 wherein said solvent is trichlorobenzene.

36. A process according to claim 34 wherein said solvent is a halogenated benzotrichloride.

* * * * *